United States Patent [19]

Smith

[11] Patent Number: 4,915,233
[45] Date of Patent: Apr. 10, 1990

[54] DENTAL ANESTHESIA ORGANIZER

[75] Inventor: Richard A. Smith, Kentfield, Calif.

[73] Assignee: The Regents of the University of California, Alameda, Calif.

[21] Appl. No.: 266,121

[22] Filed: Nov. 2, 1988

[51] Int. Cl.⁴ .................... B65D 77/22; B65D 79/00
[52] U.S. Cl. ................................ 206/571; 206/366; 206/564; 220/96
[58] Field of Search .............. 206/557, 558, 560, 561, 206/563, 564, 363, 364, 365, 366, 549, 570, 571, 572, 368, 369, 370; 220/96, 94 R

[56] References Cited

U.S. PATENT DOCUMENTS

| 928,101 | 7/1909 | Brakeman | 220/96 |
| 1,059,285 | 4/1913 | Dickinson | 206/365 |
| 1,267,810 | 5/1918 | Singleton | 220/96 |
| 2,790,547 | 4/1957 | Sutton | 206/571 |
| 3,650,393 | 3/1972 | Reiss et al. | 206/366 |
| 4,153,160 | 5/1979 | Leigh | 206/370 |
| 4,215,789 | 8/1980 | Pfeifer | 220/96 |
| 4,420,085 | 12/1983 | Wilson et al. | 206/370 X |
| 4,522,302 | 6/1985 | Paikoff | 206/364 |
| 4,523,679 | 6/1985 | Paikoff et al. | 206/570 |
| 4,595,102 | 6/1986 | Cianci et al. | 206/370 X |
| 4,657,138 | 4/1987 | Watson | 206/366 |
| 4,736,850 | 4/1988 | Bowman et al. | 206/564 X |

FOREIGN PATENT DOCUMENTS 436052 1/1912 France ....................... 206/366

Primary Examiner—William Price
Attorney, Agent, or Firm—Phillips, Moore, Lempio & Finley

[57] ABSTRACT

An organizer, particulary useful in a dental clinic practicing operative dentistry, comprises a portable tray having compartments defined thereon to retain at least one syringe, a needle encased within a protective sheath, and a hermetically sealed cartridge containing a liquid anesthetic or other liquid drug or medication adapted to be administered to a patient. In the preferred embodiment of this invention, one of the needles encased within an opened protective sheath is mounted in the same compartment as the syringe and aligned therewith whereby the syringe can be readily attached to the needle. A reciprocal finger button is mounted on the tray and has a detent engageable with the protective sheath to facilitate removal of the syringe and the attached needle from the sheath.

12 Claims, 1 Drawing Sheet

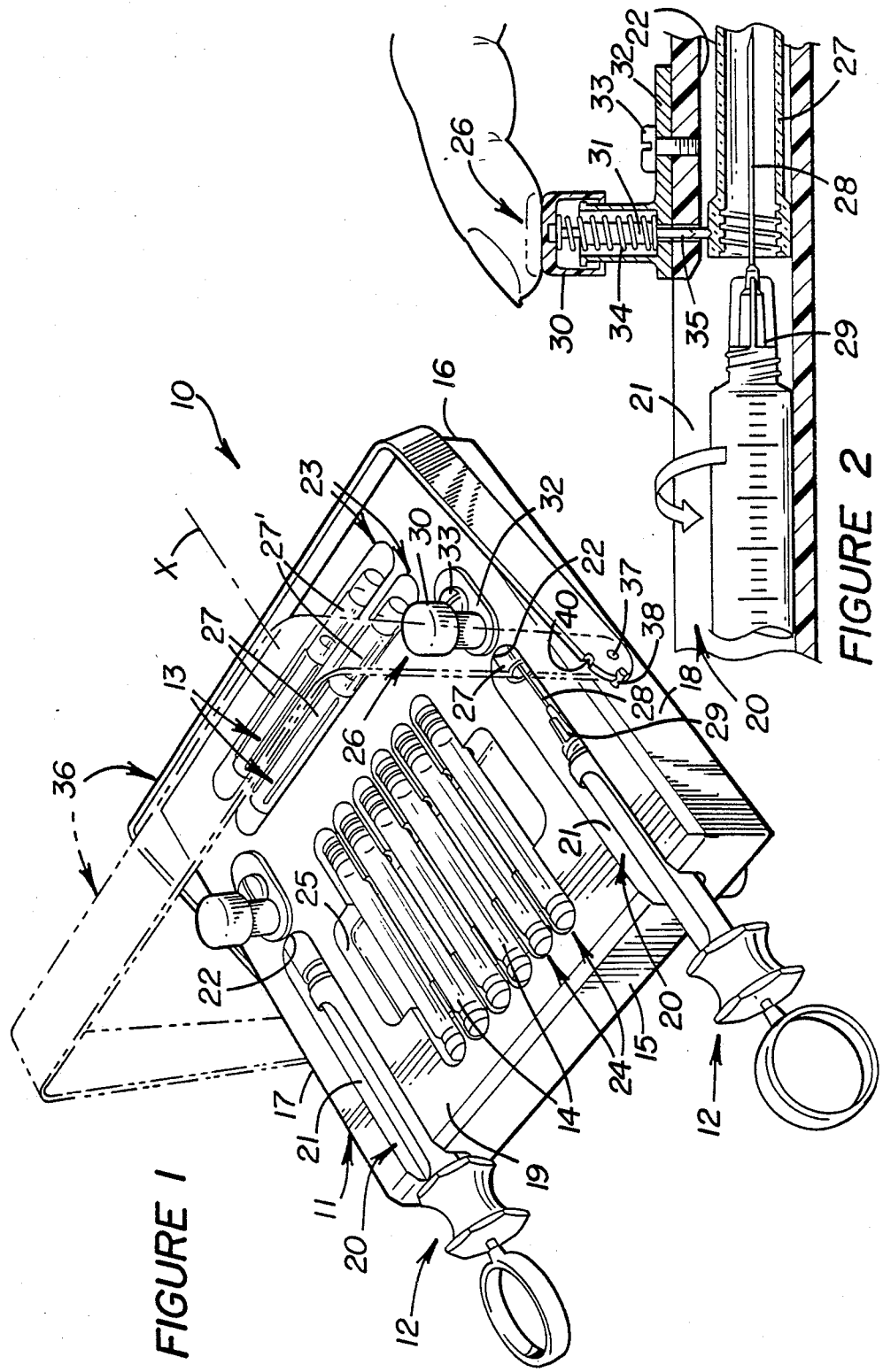

DENTAL ANESTHESIA ORGANIZER

TECHNICAL FIELD

This invention relates generally to a medical organizer for use as an armamentarium and more particularly to a dental anesthesia organizer having at least one syringe, a sheathed needle and a hermetically sealed cartridge containing a liquid anesthetic retained thereon.

BACKGROUND OF THE INVENTION

Present day practice in the dental clinics practicing operative dentistry gives rise to the possibility of needle sticks when a needle is attached to a syringe for the purpose of injecting a patient with an anesthetic. The needle is normally attached to the syringe by holding the needle and twisting or pushing the syringe onto a cap of the needle to attach them together. Although several devices have been proposed to prevent such needle sticks, such devices exhibit drawbacks.

For example, one such device includes a cardboard or plastic shield that is fitted over the protective sheath, containing the needle, when the needle is attached to the syringe. Since the user's hand is holding a shield, the user remains susceptible to a needle stick. Further, current procedures in respect to the use of syringes induces cross-contamination with no provision for safely resheathing a needle.

SUMMARY OF THE INVENTION

An object to this invention is to overcome the above, briefly described problems of the prior art by providing an economical, compact, and convenient organizer for use as an armamentarium. Although the organizer is particularly adapted for use in a clinical setting by dentists, it will become obvious to those skilled in a medical arts that the organizer will find uses in other clinical settings wherein operative surgical and related procedures are practiced.

In one aspect of this invention, the medical organizer comprises a portable tray defining a first compartment for receiving and retaining a syringe therein, a second compartment for retaining a needle and protective sheath therein, and a third compartment for retaining a hermetically sealed cartridge, containing a liquid adapted to be administered to a patient by the syringe, such as a liquid anesthetic.

In another aspect to this invention, the first compartment includes a first portion for retaining the syringe and a second portion aligned with the first portion and sized to receive and retain one of the needles and its opened protective sheath therein. Retaining means, mounted on the tray, is adapted for selectively engaging and holding the sheath in the second portion of the first compartment when the syringe is attached to the needle and then withdrawn from the first portion of such compartment. This arrangement further facilitates replacement of the syringe and attached needle on the tray to resheath the needle whereby cross-contamination and related problems are prevented.

BRIEF DESCRIPTION OF THE DRAWINGS

Other objects and advantages of this invention will become apparent from the following description and the accompanying drawings wherein:

FIG. 1 is a isometric view illustrating an organizer embodying this invention; and FIG. 2 is a sectional view illustrating the tandem relationship of a dental syringe, a needle adapted for attachment to the syringe and means for holding an opened sheath encasing the needle during such attachment.

DESCRIPTION OF THE PREFERRED EMBODIMENT

FIG. 1 illustrates an organizer 10 adapted for use as an armamentarium for the general purpose of providing a dentist with a portable unit adapted to store, transport and readily use dental anesthetics in a clinic practicing operative dentistry. In the embodiment illustrated, the organizer includes a tray 11 adapted to retain a pair of syringes 12, a pair of packaged long and short sheathed dental needles 13, and six hermetically sealed anesthetic cartridges 14 thereon for use by a dentist. Although preferably used for dental and related purposes, those skilled in the medical arts will appreciate that the organizer could likewise be used for other purposes in the field of medicine, including surgery, wherein the use of the syringes for the purpose of treating a patient is required.

Tray 11 is disposed on a longitudinal axis X thereof and exhibits proximal and distal ends 15 and 16, respectively, bounded by lateral sides 17 and 18 and a sterilizable upper surface 19. The tray may be composed of a standard moldable plastic material exhibiting the desired physical and chemical properties, such as high impact resistance and resistance to chemical deterioration. A pair of first compartments 20 are defined in upper surface 19, adjacent to lateral sides 17 and 18 of the tray, to receive and retain syringes 12 therein.

As shown in FIGS. 1 and 2, each compartment 20 comprises an elongated and exposed first compartment portion or groove 21 formed on the upper surface of the tray to terminate at an open end at proximal end 15 of the tray. As more clearly shown in FIG. 2, compartment 20 further comprises an elongated and closed second compartment portion or bore 22 aligned with a distal end of groove 21 and adapted to receive an opened, sheathed dental needle 13 therein for purposes described hereinafter.

Stored and unused packaged dental needles 13 are received and retained in a pair of second compartments 23, shown in a form of grooves defined adjacent to distal end 16 of the tray and disposed transversely relative to axis X. Anesthetic cartridges 14 are each received and retained in a third compartment 24, also defined on upper surface 19 of the tray and disposed in parallel relationship relative to first compartments 20. Compartments 24 extend in the direction of axis X, between the laterally spaced pair of first compartments 20. A generally rectangular recess 25 is preferably formed in a tray, beneath cartridges 14, to provide finger clearance for the removal thereof.

Again referring to FIGS. 1 and 2, a retaining means 26 is mounted on the tray adjacent to the distal end of each groove 21, retaining a syringe 12 therein, for selectively engaging an opened sheath 27 forming a protective plastic covering or tube for a needle 28. The sheath and needle retained in bore 22 initially form one of the illustrated packaged dental needle 13, prior to removal of a cap 27' from the sheath. The syringe is attached to a cap 29 of needle 28 in a conventional manner, i.e., by inter-engaging screw threads or by a simple press-fit. As more clearly shown in FIG. 2, retaining means 26 comprises a finger button 30 mounted on a post 31 for vertical reciprocal movement thereon. The post may be secured on a plate 32, attached to upper surface 19 of tray 11 by a screw 33, or could be formed integrally with the tray.

A compression coil spring 34 is mounted between button 30 on post 31 to normally bias the button to its raised position. As further shown in FIG. 2, a pin or detent 35 is secured to the button and extends downwardly to have its distal end exposed within bore 22, having sheath 27 retained therein. Thus, when the dentist removes syringe 12 and attached needle 28 from sheath 27, he need only depress button 30 to frictionally engage the sheath with detent 35 to hold it relative to the tray to facilitate such removal.

Referring the FIG. 1, the ease of portability of the organizer is facilitated by the use of a handle 36, mounted on the tray. The handle is adapted for movement between its illustrated collapsed, stored position along the lateral sides and distal end of the tray and its phantom-lined raised, carrying position above the tray. In the preferred embodiment of this invention, the handle is generally U-shaped and is pivotally mounted by pins 37 (one shown) on the lateral sides of the tray.

As further illustrated, means may be provided for releasably retaining the handle in its collapsed or raised position on the tray. Such means is shown in the form of a detent pin 38 secured to side 18 of the tray and the pair of shallow grooves 39 and 40, formed on the edge of the handle to alternately engage the pin. The pin and grooves can be suitably sized and the material composing the handle and/or the pin can exhibit sufficient compressibility and flexibility therebetween to permit one of the grooves to be released from the pin, upon pivoting of the handle, with the pin snapping into other groove upon alignment therewith.

I claim:

1. An organizer for use as an armamentarium to retain at least one syringe, a needle encased within a protective sheath, and a hermetically sealed cartridge, containing a liquid adapted to be administered to a patient by said syringe, said organizer comprising
    a portable tray disposed on a longitudinal axis thereof and having proximal and distal ends, lateral sides and an upper surface,
    first compartment means defined in said tray and sized for receiving and retaining said syringe therein, said first compartment means comprising an elongated and exposed first compartment portion formed as a groove on the upper surface of said tray to terminate at an open end at the proximal end of said tray and an elongated and closed second compartment portion formed generally as a bore aligned with a distal end of said groove and adapted to retain a said needle and protective sheath therein,
    second compartment means defined in said tray and sized for receiving and retaining said needle and protective sheath therein, and
    third compartment means defined in said tray and sized for retaining said cartridge therein.

2. The organizer of claim 1 wherein said first and third compartment means are disposed in parallel relationship relative to each other and extend in the direction of said axis.

3. The organizer of claim 2 wherein said second compartment means is defined adjacent to the distal end of said tray and is disposed transversely relative to said axis and each of said first and third compartment means.

4. The organizer of claim 2 wherein a pair of said first compartment means are defined adjacent to the lateral sides of said tray and wherein a plurality of said third compartment means are disposed between said pair of first compartment means.

5. The organizer of claim 1 further comprising retaining means mounted on said tray for selectively engaging and holding said sheath in said bore when said syringe is attached to said needle and then withdrawn from said groove.

6. The organizer of claim 5 wherein said retaining means comprising a detent reciprocally mounted on said tray for engagement with said sheath and means for normally biasing said detent to a retracted position, disengaging said sheath.

7. The organizer of claim 1 further comprising handle means mounted on said tray for movement between a collapsed, stored position along the lateral sides and distal end of said tray and a raised, carrying position above said tray.

8. The organizer of claim 7 wherein said handle means comprises a generally U-shaped handle pivotally mounted on the lateral sides of said tray and means for releasably retaining said handle in its collapsed or raised position on said tray.

9. The organizer of claim 1 wherein a said syringe is mounted in said first compartment portion, a said needle and protective sheath is mounted in said second compartment portion and also in said second compartment means, and said cartridge, containing a liquid anesthetic, is mounted in said third compartment means.

10. In an organizer for use as an armamentarium to retain at least one syringe and a needle disposed in a protective sheath, said needle adapted for attachment to said syringe, said organizer comprising
    a portable tray,
    compartment means in said tray forming a first compartment portion sized to receive and retain said syringe therein and a second compartment portion aligned with said first compartment portion and sized to receive and retain said needle and protective sheath therein, and
    retaining means mounted on, said tray for selectively engaging and holding said sheath in said second compartment portion when said syringe is attached to said needle and then withdrawn from the first compartment portion of said tray.

11. The organizer of claim 10 wherein said retaining means comprising a detent reciprocally mounted on said tray for engagement with said sheath and means for normally biasing said detent to a retracted position, disengaging said sheath.

12. The organizer of claim 10 or 11 wherein said first compartment portion comprises an elongated and exposed groove formed on an upper surface of said tray to terminate at an open end at a proximal end of said tray and said second compartment portion comprises an elongated and closed bore aligned with a distal end of said groove and adapted to retain said needle and protective sheath therein.

* * * * *